United States Patent [19]

Rosen et al.

[11] Patent Number: 5,512,693
[45] Date of Patent: Apr. 30, 1996

[54] PREPARATION OF TITANIUM (II) OR ZIRCONIUM (II) COMPLEXES

[75] Inventors: Robert K. Rosen, Sugar Land; Brian W. S. Kolthammer, Lake Jackson, both of Tex.

[73] Assignee: The Dow Chemical Company, Midland, Mich.

[21] Appl. No.: 350,924

[22] Filed: Dec. 7, 1994

[51] Int. Cl.$^6$ ............................... C07F 17/00; C07F 7/28
[52] U.S. Cl. ........................ 556/7; 556/11; 556/12; 556/14; 556/19; 556/28; 556/52; 556/56; 502/103; 502/152; 502/155; 526/126; 526/127
[58] Field of Search ............................. 556/7, 11, 12, 556/14, 19, 28, 52, 56

[56] References Cited

U.S. PATENT DOCUMENTS

| | | | |
|---|---|---|---|
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,153,157 | 10/1992 | Hlatky et al. | 502/117 |
| 5,198,401 | 3/1993 | Turner et al. | 502/155 |
| 5,372,682 | 12/1994 | Devore et al. | 204/72 |

FOREIGN PATENT DOCUMENTS

| | | |
|---|---|---|
| 277003 | 8/1988 | European Pat. Off. |
| 416815 | 3/1991 | European Pat. Off. |
| 468651 | 1/1992 | European Pat. Off. |
| 520732 | 12/1992 | European Pat. Off. |
| 93/19104 | 9/1993 | WIPO . |

OTHER PUBLICATIONS

Yasuda, et al., *Organometallics*, 1, 388 (1982) (Yasuda I).
Yasuda, et al., *Acc. Chem. Res.*, 18, 120 (1985) (Yasuda II).
Erker, et al., *Adv. Organomet. Chem.*, 24, 1 (1985).
Yamamoto et al., *Organometallics*, 8, 105 (1989).
Blenkers, J, et al., *Organometallics*, 6, 459 (1987).

*Primary Examiner*—Porfirio Nazario-Gonzales

[57] ABSTRACT

Titanium and zirconium complexes comprising a single, cyclic, delocalized n-bonded ligand group wherein the metal of said complexes is in the +2 formal oxidation state are prepared in high yield and purity by reaction of titanium and zirconium halides in the +3 or +4 oxidation state with an n-alkyl Grignard reagent. The complexes are used as catalyst components for α-olefin polymerization catalysts.

13 Claims, No Drawings

PREPARATION OF TITANIUM (II) OR ZIRCONIUM (II) COMPLEXES

BACKGROUND OF THE INVENTION

This invention relates to a process for preparing certain titanium and zirconium complexes comprising a single, cyclic, delocalized n-bonded ligand group wherein the metal of said complexes is in the +2 formal oxidation state. More particularly, this invention relates to such processes wherein the metal is covalently bonded to the cyclic group via the delocalized n-system and also covalently bonded thereto via a divalent ligand group. Such complexes are referred to in the art as "constrained geometry" complexes.

The preparation and characterization of certain biscyclopentadienyl zirconium and hafnium diene complexes are described in the following references: Yasuda, et al., *Organometallics*, 1, 388 (1982) (Yasuda I); Yasuda, et al., *Acc. Chem. Res.*, 18, 120 (1985), (Yasuda II); Erker, et al., *Adv. Organomet. Chem.*, 24, 1 (1985); and U.S. Pat. No. 5,198, 401. The preparation of certain Ti, Zr, and Hf monocyclopentadienyl diene complexes lacking the present bridged ligand structure, was described in Yamamoto et al., *Organometallics*, 8, 105 (1989) (Yamamoto) and Blenkers, J, et al., *Organometallics*, 6, 459 (1987).

Constrained geometry metal complexes, including titanium complexes, and methods for their preparation are disclosed in U.S. application Ser. No. 545,403, filed Jul. 3, 1990 (EP-A-416,815); U.S. application Ser. No. 547,718, filed Jul. 3, 1990 (EP-A-468,651); U.S. application Ser. No. 702,475, filed May 20, 1991 (EP-A-514,828); U.S. application Ser. No. 876,268, filed May 1, 1992, (EP-A-520,732) and U.S. application Ser. No. 8,003, filed Jan. 21, 1993 (WO93/19104), as well as U.S. Pat. No. 5,055,438, U.S. Pat. No. 5,057,475, U.S. Pat. No. 5,096,867, U.S. Pat. No. 5,064,802 and U.S. Pat. No. 5,132,380.

SUMMARY OF THE INVENTION

According to one embodiment of the present invention there is provided a process for preparing a metal complex containing one and only one cyclic, delocalized n-bonded group, said complex corresponding to the formula:

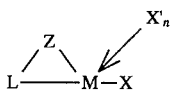

wherein,

M is titanium or zirconium in the +2 formal oxidation state;

L is a group containing a cyclic, delocalized, anionic, n-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 non-hydrogen atoms;

X is a neutral, conjugated diene, optionally substituted with one or more hydrocarbyl groups, said X having up to 40 carbon atoms and forming a n-complex with M;

X' is a neutral Lewis base ligand selected from amines, phosphines and ethers said X' having from 3 to 20 non-hydrogen atoms; and n is a number from 0 to 3;

said process comprising contacting a metal halide compound according to the formula

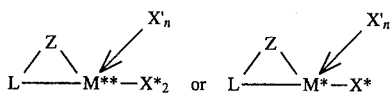

wherein,

M* is titanium or zirconium in the +3 formal oxidation state;

M** is titanium or zirconium in the +4 formal oxidation state;

X* is halide; and

L, Z, X' and n are as previously defined;

with a free diene corresponding to X, and subsequently or simultaneously contacting the resulting reaction mixture with a Grignard derivative of a $C_{1-20}$ n-alkane to form the desired metal complex.

According to a second embodiment of the present invention there is also provided a process for first preparing the above starting cyclic complexes in situ. Thus, there is provided a process for preparing a metal complex containing one and only one cyclic, delocalized n-bonded group, said complex corresponding to the formula:

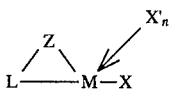

wherein,

M is titanium or zirconium in the +2 formal oxidation state;

L is a group containing a cyclic, delocalized, anionic, n-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 non-hydrogen atoms;

X is a neutral, conjugated diene, optionally substituted with one or more hydrocarbyl groups, said X having up to 40 carbon atoms and forming a n-complex with M;

X' is a neutral Lewis base ligand selected from amines, phosphines and ethers said X' having from 3 to 20 non-hydrogen atoms; and n is a number from 0 to 3;

said process comprising:

1) contacting a metal halide compound according to the formula $M^*(X^*)_3X'_n$ or $M^{**}(X^*)_4X'_n$, wherein;

M* is titanium or zirconium in the +3 formal oxidation state;

M** is titanium or zirconium in the +4 formal oxidation state; and

X* is halide;

with a dianionic salt corresponding to the formula: $M'_2LZ$, wherein;

M' is a Group 1 metal, MgCl or MgBr or two M' groups together are a Group 2 metal;

to form an intermediate metal complex according to the formula:

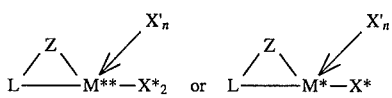

wherein L, Z, M**, X*, X', M* and n are as previously defined;

2) when the metal in said intermediate metal complex is in the +3 formal oxidation state, optionally contacting said intermediate metal complex with an oxidant to form an intermediate metal complex according to the formula:

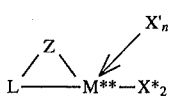

wherein L, Z, M**, X*, X', and n are as previously defined; and 3) contacting the intermediate metal complex with a free diene corresponding to X, and subsequently or simultaneously contacting the resulting reaction mixture with a Grignard derivative of a $C_{1-20}$ n-alkane to form the desired metal complex.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The diene group, X, does not decompose under reaction conditions used to prepare the complexes of the invention. Under subsequent polymerization conditions, or in the formation of catalytic derivatives of the present complexes, the diene group, X, may undergo chemical reactions or be replaced by another ligand.

The present titanium and zirconium complexes contain a neutral diene ligand which is coordinated via n-complexation through the diene double bonds, and not through a metallacycle containing σ-bonds (σ-bound diene) where the metal is in the +4 formal oxidation state. Such a distinction is readily determined by X-ray crystallography or by NMR spectral characterization according to the techniques of Yasuda I, Yasuda II, and Erker, et al., Supra, as well as the references cited therein. By the term "n-complex" is meant both the donation and back acceptance of electron density by the ligand are accomplished using ligand n-orbitals, i.e., the diene is n-bound (n-bound diene).

A suitable method of determining the existence of a n-complex in conjugated diene containing metal complexes is the measurement of metal-carbon atomic spacings for the carbons of the conjugated diene using common X-ray crystal analysis techniques. Measurements of atomic spacings between the metal and C1, C2, C3, C4 (M-C1, M-C2, M-C3, M-C4, respectively) (where C1 and C4 are the terminal carbons of the 4 carbon conjugated diene group and C2 and C3 are the internal carbons of the of the 4 carbon conjugated diene group) may be made. If the difference between these bond distances, Δd, using the following formula:

$$\Delta d = \left[ \left\{ \frac{(M-C1)+(M-C4)}{2} \right\} - \left\{ \frac{(M-C2)+(M-C3)}{2} \right\} \right]$$

is greater than −0.15 Å, the diene is considered to form a n-complex with M. In the use of such X-ray crystal analysis techniques at least "good" and preferably "excellent" determination quality as defined by G. Stout et al., *X-ray Structure Determination, A Practical Guide.*, Macmillan Co., pg 430–431 (1968) is used.

Examples wherein the above method for determination of n-complexes has been applied to prior art compounds are found in Erker, et al., *Angew. Chem, Int. Ed. Eng.*, 23, 455–456 (1984) (Erker et al.) and Yamamoto, Supra. In the former reference ($\eta^3$-allyl)($\eta^4$-butadiene) ($\eta^5$-cyclopentadienyl)zirconium was crystallographically characterized. The M-C1 and M-C4 distances were both 2.360 (±0.005) Å. The M-C2 and M-C3 distances were both 2.463 (±0.005) Å, giving a Δd of −0.103 Å. In the latter reference ($\eta^5$-pentamethylcyclopentadienyl)($\eta^4$-1,4-diphenyl-1,3-butadiene)titanium chloride was shown to have M-C1 and M-C4 distances of 2.233 (±0.006) Å. The M-C2 and M-C3 distances were both 2.293 (±0.005) Å, giving a Δd of −0.060 Å. Erker et al. also disclosed bis(cyclopentadienyl)zirconium (2,3-dimethyl-1,3-butadiene). In this complex the M-C1 and M-C4 distances were 2.300 Å. The M-C2 and M-C3 distances were both 2.597 Å, giving a Δd of −0.297 Å. Accordingly, this complex contains a σ-bound diene and the zirconium is in the +4 formal oxidation state.

Alternatively, complexes of the present invention wherein X is a conjugated diene in the form of a n-complex and M is in the +2 formal oxidation state are identified using nuclear magnetic resonance spectroscopy techniques. The teachings of Erker, et al., Supra., C. Krüger, et al. *Organometallics*, 4, 215–223, (1985), and Yasuda I, Supra, disclose these well known techniques for distinguishing between n-bound complexes and metallocyclic coordination or σ-bound diene complexes.

The reactions of this invention may be conducted at temperatures from −100° C. to 300° C., preferably from 0° to 80° C. Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and styrene, alkyl ethers having from 1 to 4 carbons in each alkyl group; $C_{1-4}$ dialkyl ether derivatives of (poly)alkylene glycols, and tetrahydrofuran. Mixtures of the foregoing are also suitable.

The process generates the desired metal complex in high yields and efficiencies due to the fact that the n-alkyl Grignard reagent is much more efficient in conversion of the halide precursors than are secondary or tertiary alkyl Grignard reagents. Without wishing to be bound by any particular theory, it is believed that in the presence of the conjugated diene reactant, a Group 4 metal complex is formed upon reaction of the precursor metal halide with the n-alkyl Grignard reagent which is reduced to the +2 oxidation state in situ. Thus, the process achieves high yields of the desired complex wherein the Group 4 metal is in the +2 formal oxidation state without the addition of conventional reducing agents, such as Group 1 or 2 metals or amalgams such as Hg/Na or K/Na. Moreover, in a preferred embodiment, the reaction is conducted in a polar aprotic solvent, especially an aliphatic ether, most preferably diethylether, tetrahydrofuran (THF) or dimethoxyethane (DME). In such solvents the Grignard reagent is relatively soluble. This allows for the use of nonpolar solvents, especially hydrocarbons, in which Grignard reagents and metal salt byproducts are relatively insoluble, to be used to recover the desired reaction product.

All of the steps of the reaction may be performed in sequence in a single reactor vessel without isolation of intermediate products, thereby greatly assisting in the large scale, commercial practice of the process. The recovery procedure usually involves separation of the resulting salt byproducts and unreacted Grignard reagent and devolatilization of the reaction medium. As previously mentioned, extraction into a secondary solvent, especially an alkane, is highly desired.

The relative amounts of the respective reagents are not critical to the process, but generally, stoichiometric amounts are employed for the most economical operation. Specifically, the amount of Grignard reagent used is desirably in a molar ratio from 1:1 to 3:1 compared to the amount of metal halide to be converted, depending on the formal oxidation state of the intermediate metal halide. The amount of diene reagent used is desirably in a molar ratio from 1:1 to 30:1, preferably in a molar ratio from 1:1 to 10:1, compared to the amount of intermediate metal complex.

Preferred neutral Lewis bases include pyridine, diethylether, tetrahydrofuran (THF), 1,2-dimethoxyethane (DME), or tetramethylethylenediamine (TMEDA). The Grignard complex (either the derivative of —LZ— or of the n-alkane) may also be in the form of an adduct, such as the DME or THF coordinated Grignard adduct.

In the optional oxidation step performed in the alternative embodiment of the invention, any suitable oxidant may be employed. Preferred oxidants are halogenated $C_{1-10}$ organic compounds, especially halogenated $C_{1-10}$ alkanes, such as 1,2-dichloroethane or chloroform, which uniquely undergo one electron oxidations incorporating only the halide group into the metal complex. Use of such halogenated organic oxidants in this manner is further disclosed in EP-A-514,828 (equivalent to U.S. Ser. No. 07/967,365), the teachings of which are incorporated herein by reference.

Inasmuch as the complexes can contain only one cyclic delocalized, anionic, n-bonded group, it follows that Z or X, singly or in combination, cannot comprise a cyclopentadienyl group or other cyclic delocalized n-bonded group.

Preferred metal coordination complexes prepared according to the present invention correspond to the formula:

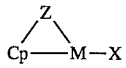

wherein Z, M and X are as previously defined; and

Cp is a $C_5H_4$ group bound to Z and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 nonhydrogen atoms, and optionally, one or two pairs of such substituents together form a $C_{2-10}$ hydrocarbylene group, thereby causing Cp to have a fused ring structure.

More preferred metal coordination complexes prepared according to the present invention correspond to the formula:

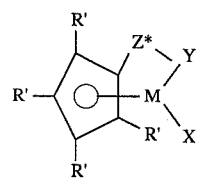

wherein:

R' each occurrence is independently selected from hydrogen, hydrocarbyl, silyl, germyl, halo, cyano, and combinations thereof, said R' having up to 20 nonhydrogen atoms, and optionally, one or two pairs of such substituents together each form a $C_{2-10}$ hydrocarbylene group, thereby causing Cp to have a fused ring structure;

X is a neutral $\eta^4$-bonded, conjugated diene group having up to 30 non-hydrogen atoms, which forms a n-complex with M;

Y is —O—, —S—, —NR*—, —PR*—;

M is titanium or zirconium in the +2 formal oxidation state;

Z* is SIR*$_2$, CR*$_2$, SiR*$_2$SiR*$_2$, CR*$_2$CR*$_2$, CR*=CR*, CR*$_2$SiR*$_2$, or GeR*$_2$; wherein:

R* each occurrence is independently hydrogen, or a member selected from hydrocarbyl, silyl, halogenated alkyl, halogenated aryl, and combinations thereof, said R* having up to 10 non-hydrogen atoms.

Preferably, R' independently each occurrence is hydrogen, hydrocarbyl, silyl, halo or a combination thereof, said R' having up to 10 non-hydrogen atoms, or one or two pairs of adjacent R' substituents together each form a $C_{2-10}$ hydrocarbylene group, thereby causing Cp to have a fused ring structure. Most preferably, R' is hydrogen, methyl, ethyl, propyl, butyl, pentyl, hexyl, (including where appropriate all isomers), cyclopentyl, cyclohexyl, norbornyl, benzyl, or phenyl or one or two pairs of adjacent R' substituents together cause the entire $C_5R'_4$ group to be an indenyl, tetrahydroindenyl, fluorenyl, tetrahydrofluorenyl, or octahydrofluorenyl group.

Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ hydrocarbyl.

Examples of suitable X groups include: $\eta^4$-1,3-pentadiene; $\eta^4$-2,4-hexadiene; $\eta^4$-1,4-diphenyl-1,3-butadiene; $\eta^4$-3-methyl-1,3-pentadiene; $\eta^4$-1,4-dibenzyl-1,3-butadiene; $\eta^4$-1,4-ditolyl-1,3-butadiene; $\eta^4$-1,4-bis(trimethylsilyl)-1,3-butadiene, $\eta^4$-1-(4-t-butylphenyl)-4-phenyl-1,3-butadiene, $\eta^4$-1-(3-methylphenyl)-4-phenyl-1,3-butadiene, and $\eta^4$-1-(3-methoxyphenyl)-4-phenyl-1,3-butadiene.

Most highly preferred metal coordination complexes prepared according to the present invention are amidosilane- or amidoalkanediyl- compounds corresponding to the formula:

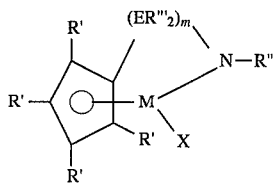

wherein:

M is titanium;

X is $\eta^4$-1,3-pentadiene, $\eta^4$-2,4-hexadiene, $\eta^4$-1,4-diphenyl-1,3-butadiene, $\eta^4$-3-methyl-1,3-pentadiene, $\eta^4$-1,4-dibenzyl-1,3-butadiene, $\eta^4$-1,4-ditolyl-1,3-butadiene, or $\eta^4$-1,4-bis(trimethylsilyl)-1,3-butadiene;

R' is hydrogen or methyl, or one or two pairs of R' groups together cause the ring structure to be an indenyl, tetrahydroindenyl, fluorenyl or octahydrofluorenyl group;

R" is $C_{1-10}$ hydrocarbyl;

R''' is independently each occurrence hydrogen or $C_{1-10}$ hydrocarbyl;

E is independently each occurrence silicon or carbon; and m is 1 or 2.

Examples of the most highly preferred metal complexes prepared according to the present invention include compounds wherein R" is methyl, ethyl, propyl, butyl, pentyl, hexyl, (including all isomers of the foregoing where applicable), cyclododecyl, norbornyl, benzyl, or phenyl; $(ER'''_2)_m$ is dimethylsilane, or ethanediyl; and the cyclic delocalized n-bonded group is cyclopentadienyl, tetramethylcyclopentadienyl, indenyl, tetrahydroindenyl, fluorenyl, tetrahydrofluorenyl or octahydrofluorenyl.

Highly preferred diene compounds are: 1,3-pentadiene; 2,4-hexadiene; 1,4-diphenyl-1,3-butadiene; 3-methyl-1,3-pentadiene; 1,4-dibenzyl-1,3-butadiene; 1,4-ditolyl-1,3-butadiene; 1,4-bis(trimethylsilyl)-1,3-butadiene, 1-(4-t-butylphenyl)-4-phenyl-1,3-butadiene, 1-(3-methylphenyl)-4-phenyl-1,3-butadiene, and 1-(3-methoxyphenyl)-4-phenyl-1,3-butadiene. All positional and geometric isomers of the foregoing diene reactants may be utilized.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, such as, $C_{1-30}$ hydrocarbyl substituted Group 13 compounds, especially tri(hydrocarbyl)aluminum- or tri(hydrocarbyl)boron compounds and halogenated derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, inert, compatible, noncoordinating, ion forming compounds (including the use of such compounds under oxidizing conditions); bulk electrolysis; and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A- 468,651 (equivalent to U.S. Ser. No. 07/547,718), EP-A- 520,732 (equivalent to U.S. Ser. No. 07/876,268), EP-A-520,732 (equivalent to U.S. Ser. No. 07/884,966 filed May 1, 1992) and U.S. Pat. No. 5,372,682 the teachings of which are herein incorporated by reference.

Combinations of strong Lewis acids, especially the combination of a trialkylaluminum compound having from 1 to 4 carbons in each alkyl group and a halogenated tri(hydrocarbyl)boron compound having from 1 to 10 carbons in each hydrocarbyl group, especially tris(pentafluorophenyl)borane, further combinations of such strong Lewis acid mixtures with a polymeric or oligomeric alumoxane, and combinations of a single strong Lewis acid, especially tris(pentafluorophenyl)borane with a polymeric or oligomeric alumoxane are especially desirable activating cocatalysts.

The catalysts are suitably employed in the polymerization of olefins according to known Ziegler-Natta polymerization conditions. Especially suited are polymerization temperatures from 0°–250° C. and pressures from atmospheric to 1000 atmospheres (0.1 to 100 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase or slurry polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for solution polymerizations are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), 4-vinylcyclohexene, and vinylcyclohexane. Mixtures of the foregoing are also suitable.

The skilled artisan will appreciate that the invention disclosed herein may be practiced in the absence of any component which has not been specifically disclosed. Having described the invention the following examples are provided as further illustration thereof and are not to be construed as limiting. Unless stated to the contrary all parts and percentages are expressed on a weight basis.

EXAMPLE 1

Preparation of
(t-butylamido)(tetramethyl-$\eta^5$-cyclopentadienyl)-
dimethylsilanetitanium 1,3-pentadiene A. from (t-butylamido)(tetramethyl-$\eta^5$-cyclopentadienyl)dimethylsilanetitaniumdichloride and n-BuMgCl in refluxing DME In an inert atmosphere glove box, 0.25 g (0.68 mmol) of $C_5Me_4SiMe_2NCMe_3TiCl_2$ ((t-butylamido)(tetramethyl-$\eta^5$-cyclopentadienyl)dimethylsilanetitanium dichloride) was dissolved into 20 mL of 1,2-dimethoxyethane (DME). To this solution was added 0.34 mL (3.39 mmol) of 1,3-pentadiene followed by 1.02 mL of 2M n-BuMgCl in diethylether (2.04 mmol). The mixture's color changed to a deep purple color. The reaction mixture was heated to reflux for one hour then cooled to ambient temperature (20° C.) and the volatile materials removed under reduced pressure. The solid residue was extracted with pentane and the extract filtered. The pentane was removed under reduced pressure leaving purple/black microcrystals of the desired product (Formula A), which was identified by $^1$H NMR analysis. Yield was 0.21 g., 84 percent.

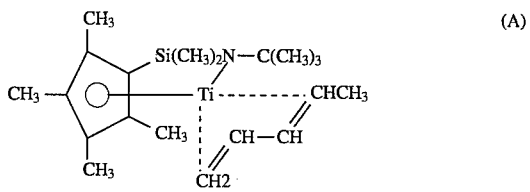

B. from (t-butylamido)(tetramethyl-$\eta^5$-cyclopentadienyl)dimethylsilanetitaniumdichloride and n-BuMgCl in DME at 40 ° C.

The reaction conditions of Example 1A were substantially repeated excepting that 0.50 g. (1.36 mmol) of $C_5Me_4SiMe_2NCMe_3TiCl_2$, 25 mL of DME, 0.68 mL (6.79 mmol) of 1,3-pentadiene and 2.04 mL of 2M n-BuMgCl in diethylether (4.07 mmol) were used. The reactants were combined in a Schlenk tube, the tube was sealed, removed to a Schlenk line, vented to a nitrogen bubbler and immersed in an oil bath maintained at 40° C. After two hours the tube was returned to the drybox, where the residue was extracted with pentane filtered and recovered. Product purity was extremely high. Yield was 0.37 g., 74 percent.

C. from (t-butylamido)(tetramethyl-$\eta^5$-cyclopentadienyl)dimethylsilanetitaniumdichloride and n-BuMgCl in DME at 20 ° C.

The reaction conditions of Example 1A were substantially repeated excepting that 0.25 g (0.68 mmol) of (t-butylamido)(tetramethyl-$\eta^5$-cyclopentadienyl)dimethylsilanetitaniumdichloride, 0.35 mL (13.58 mmol) of 1,3-pentadiene, and 1.018 mL (2.04 mmol) of n-BuMgCl were used and the reaction mixture was stirred for three hours at ambient temperature (20° C.). Product purity was extremely high.

EXAMPLE 2

Preparation of
(t-butylamido)(tetramethyl-$\eta^5$-cyclopentadienyl)-
dimethylsilanetitanium 1,3-pentadiene from
$TiCl_3.3THF$ and n-BuMgCl in refluxing DME In an inert atmosphere glove box, 1.0 g. of $C_5Me_4SiMe_2NCMe_3[MgCl]_2.n$ DME having an effective molecular weight by titration of 514 g/mol (1.95 mmol) was placed in a 100 mL flask with 20 mL of DME. $TiCl_3.3THF$ (0.72 g, 1.95 mmol) was added and the mixture stirred for 15 minutes. $CH_2CH_2$ (75 μL (1.17 mmol)) was added causing the color to become reddish brown. After 30 minutes, 3.9 mL of 1,3-pentadiene (38.91 mmol) was added followed by 2.9 mL of 2M n-BuMgCl (5.84 mmol) in diethylether. The mixture's color changed to a deep purple color. The reaction mixture was heated to reflux for one hour then cooled to ambient temperature (20° C.) and the volatile materials removed under reduced pressure. The solid residue was extracted with pentane and the extract filtered. The pentane was removed under reduced pressure leaving purple/black microcrystals of the desired product, which was identified by 1H NMR analysis to be highly pure.

EXAMPLE 3

Large Scale Preparation of
(t-butylamido)(tetramethyl-$\eta^5$-cyclopentadienyl)-
dimethylsilanetitanium 1,3-pentadiene from
$TiCl_3 \cdot 1.5$ DME and n-BuMgCl A) Preparation of $TiCl_3 \cdot 1.5$ (DME)

A 10 L glass kettle (R-1) with flush mounted bottom valve, 5-neck head, teflon gasket, clamp, and stirrer components (bearing, shaft, and paddle) was set up in the hood and purged with nitrogen. The necks were equipped as follows: stirrer components were located on the center neck, and the outer necks had a reflux condenser topped with gas inlet/outlet, an inlet for solvent, a thermocouple, and a stopper, respectively. Dry, deoxygenated dimethyoxyethane (DME) was added to the flask (approx. 4.3 L). In the drybox, 322 g of $TiCl_3$ was weighed into an equalizing powder addition funnel; the funnel was capped, removed from the drybox, and put on the reaction kettle in place of the stopper. The $TiCl_3$ was added over about 10 minutes with stirring. After the addition was completed, additional DME was used to wash the rest of the $TiCl_3$ into the flask. The addition funnel was replaced with a stopper, and the mixture heated to reflux. The color changed from purple to pale blue. The mixture was heated for about 4.5 hours. It was then cooled to room temperature, the solid was allowed to settle, and the supernatant was decanted from the solid. The product, $TiCl_3 \cdot 1.5$ (DME) remained in the reactor as a pale blue solid.

B) Preparation of $[(Me_4C_5)SiMe_2N^tBu][MgCl]_2$

A 30 L glass kettle (R-2) with flush mounted bottom valve, 7-neck head, teflon gasket, clamp, and stirrer components (bearing, shaft, and paddle) was set up in the hood and purged with nitrogen. The head was equipped with stirrer in the center neck, and the outer necks containing a condenser, nitrogen inlet/outlet, vacuum adapter, reagent addition tube, thermocouple, and stoppers respectively. The reactor was loaded with 525 g of $(Me_4C_5H)SiMe_2NH^tBu$, followed by 5 L of toluene, and then 1.57 kg of 2.2M i-PrMgCl in diethylether. The mixture was then heated, and the ether allowed to boil off into a trap cooled to −78° C. The inner thermocouple temperature reached a maximum of 85° C. after 2 hours of heating. At the end of this time, the heater was turned off, and DME was added to the hot, stirring solution, resulting in the precipitation of a white solid. The mixture was then heated again to an inner temperature of 85° C. and held there for an additional hour. The solution was allowed to cool to room temperature, the material was allowed to settle, and the supernatant was decanted from the solid. An additional wash was done by adding toluene, stirring for several minutes, allowing the solids to settle, and decanting the toluene solution. The product, $[(Me_4C_5)SiMe_2N^tBu][MgCl]_2$, was left in R-2 as an off-white, solvated solid.

C) Preparation of $[(Me_4C_5)SiMe_2N^tBu]Ti(1,3$-pentadiene)

The materials in R-1 and R-2 were slurried in DME (the total volumes of the mixtures were approximately 3.7 L in R-1 and 12 L in R-2). The contents of R-1 were transferred into R-2 using a transfer tube connected to the bottom valve of the 10 L flask and one of the head openings in the 30 L flask. The remaining material in R-1 was washed over using additional DME. The mixture darkened quickly to a deep red/brown color. After 30 minutes, 73 mL of $CH_2Cl_2$ was added through a dropping funnel, resulting in a color change to green/brown. After approximately 2 hours, 640 g of 1,3-pentadiene was added, followed by 2.26 kg of 2 M nBuMgCl in THF. The mixture was warmed to 40° C. and stirred at this temperature for 2 hours. Then approximately 7.5 L of solvent was removed under vacuum. Isopar E™ (approx. 5.3 L) (available from Exxon Chemical Co.) was then added to the flask. This vacuum/solvent addition cycle was repeated, with approx. 5.7 L of solvent removed and 4.3 L of Isopar E™ added. The material was allowed to settle, then the liquid layer was decanted into another 30 L glass kettle (R-3). The solids in R-2 were washed with additional Isopar E; this solution was combined with the first decant in R-3. The solvent in R-3 was removed under vacuum to leave a red/black solid, which was reextracted with Isopar E™. This material was transferred into a storage cylinder. Analysis indicated that the solution (9.39 L) was 0.1360 M in titanium. Thus the yield was equal to 467 g (1,277 moles) of $[(Me_4C_5)SiMe_2N^tBu]Ti(1,3$-pentadiene), 61 percent based on $TiCl_3$.

EXAMPLE 4

Synthesis from $TiCl_3 \cdot 3$ THF Without Oxidation Using $CH_2Cl_2$

In the drybox, 1.0 g of $[(Me_4C_5)SiMe_2N^tBu][MgCl]_2$ $[DME]_n$ (effective molecular weight by titration: 514 g/mol) was placed in a 100 mL flask with 20 mL of DME. $TiCl_3 \cdot 3$ THF (0.72 g) was added using 10 mL of additional DME. The mixture was stirred for 15 minutes, then 0.97 mL of 1,3-pentadiene was added followed by 1.46 mL of 2M nBuMgCl in THF. The color changed to a deep red/purple. The mixture was stirred for one hour. At the end of this time, the volatile materials were removed under reduced pressure. The residue was extracted with pentane, the solution was filtered, and the pentane was removed under reduced pressure to leave a dark purple/black solid. The $^1H$ NMR spectrum of this material indicated it to be pure $[(Me_4C_5)SiMe_2N^tBu]Ti(1,3$-pentadiene). The yield was 0.52 g, 73 percent.

What is claimed is:

1. A process for preparing a metal complex containing one and only one cyclic, delocalized n-bonded group, said complex corresponding to the formula:

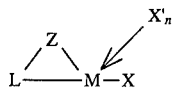

wherein,

M is titanium or zirconium in the +2 formal oxidation state;

L is a group containing a cyclic, delocalized, anionic, n-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 non-hydrogen atoms;

X is a neutral, conjugated diene, optionally substituted with one or more hydrocarbyl groups, said X having up to 40 carbon atoms and forming a n-complex with M;

X' is a neutral Lewis base ligand selected from amines, phosphines and ethers said X' having from 3 to 20 non-hydrogen atoms; and n is a number from 0 to 3;

said process comprising contacting a metal halide compound corresponding to the formula

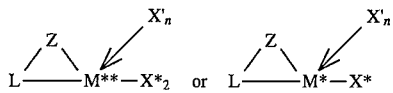

wherein,

M* is titanium or zirconium in the +3 formal oxidation state;

M** is titanium or zirconium in the +4 formal oxidation state;

X* is halide; and

L, Z, X' and n are as previously defined;

with a free diene corresponding to X, and subsequently or simultaneously contacting the resulting reaction mixture with a Grignard derivative of a $C_{1-20}$ n-alkane to form the desired metal complex.

2. A process for preparing a metal complex containing one and only one cyclic, delocalized n-bonded group, said complex corresponding to the formula:

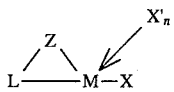

wherein,

M is titanium or zirconium in the +2 formal oxidation state;

L is a group containing a cyclic, delocalized, anionic, n-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 non-hydrogen atoms;

X is a neutral, conjugated diene, optionally substituted with one or more hydrocarbyl groups, said X having up to 40 carbon atoms and forming a n-complex with M;

X' is a neutral Lewis base ligand selected from amines, phosphines and ethers said X' having from 3 to 20 non-hydrogen atoms; and n is a number from 0 to 3;

said process comprising:

1) contacting a metal halide compound according to the formula $M*(X*)_3X'_n$ or $M**(X*)_4X'_n$, wherein;

M* is titanium or zirconium in the +3 formal oxidation state;

M** is titanium or zirconium in the +4 formal oxidation state; and

X* is halide;

with a dianionic salt corresponding to the formula: $M'_2LZ$, wherein;

M' is a Group 1 metal, MgCl or MgBr or two M' groups together are a Group 2 metal;

to form an intermediate metal complex according to the formula:

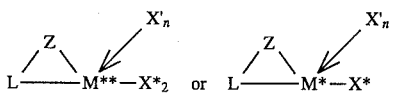

wherein L, Z, M**, X*, X', M* and n are as previously defined;

2) when the metal in said intermediate metal complex is in the +3 formal oxidation state, optionally contacting said intermediate metal complex with an oxidant to form an intermediate metal complex according to the formula:

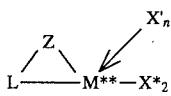

wherein L, Z, M**, X*, X' and n are as previously defined; and 3) contacting the intermediate metal complex with a free diene corresponding to X, and subsequently or simultaneously contacting the resulting reaction mixture with a Grignard derivative of a $C_{1-20}$ n-alkane to form the desired metal complex.

3. A process according to either claim 1 or 2 wherein the free diene corresponding to X is 1,4-diphenyl- 1,3-butadiene; 1,3-pentadiene; 1,4-dibenzyl- 1,3-butadiene; 2,4-hexadiene; 3-methyl-1,3-pentadiene; 1,4-ditolyl-1,3-butadiene; or 1,4-bis(trimethylsilyl)-1,3-butadiene.

4. A process according to either claim 1 or 2 wherein X is 1,3-pentadiene.

5. A process according to either claim 1 or 2 wherein the resulting metal complex corresponds to the formula:

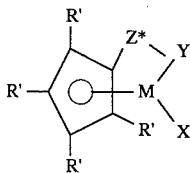

wherein:

R' each occurrence is independently selected from hydrogen, hydrocarbyl, silyl, germyl, halo, cyano, and combinations thereof, said R' having up to 20 nonhydrogen atoms, and optionally, one or two pairs of such substituents together each form a $C_{2-10}$ hydrocarbylene group, thereby causing Cp to have a fused ring structure;

X is a neutral $\eta^4$-bonded diene group having up to 30 non-hydrogen atoms, which forms a n-complex with M;

Y is —O—, —S—, —NR*—, —PR*—;

M is titanium or zirconium in the +2 formal oxidation state;

Z* is $SIR*_2$, $CR*_2$, $SiR*_2SiR*_2$, $CR*_2CR*_2$, $CR*=CR*$, $CR*_2SiR*_2$, or $GeR*_2$; wherein:

R* each occurrence is independently hydrogen, or a member selected from hydrocarbyl, silyl, halogenated alkyl, halogenated aryl, and combinations thereof, said R* having up to 10 non-hydrogen atoms.

6. A process according to claim 5 wherein R' independently each occurrence is hydrogen, hydrocarbyl, silyl, halo or a combination thereof, said R' having up to 10 non-hydrogen atoms, or one or two pairs of adjacent R' substituents together each form a $C_{2-10}$ hydrocarbylene group, thereby causing Cp to have a fused ring structure.

7. A process according to claim 6 wherein R' is hydrogen, methyl, ethyl, propyl, butyl, pentyl, hexyl, (including where appropriate all isomers), cyclopentyl, cyclohexyl, norbornyl, benzyl, or phenyl or one or two pairs of adjacent R' substituents together cause the entire $C_5R'_4$ group to be an indenyl, tetrahydroindenyl, fluorenyl, tetrahydrofluorenyl, or octahydrofluorenyl group.

8. A process according to claim 5 wherein Y is a nitrogen or phosphorus containing group corresponding to the formula —N(R")— or —P(R")—, wherein R" is $C_{1-10}$ hydrocarbyl.

9. A process according to claim 5 wherein the metal complex corresponds to the formula:

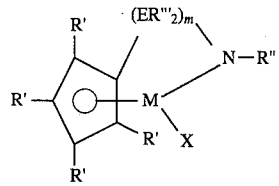

wherein:

M is titanium;

X is $\eta^4$-1,3-pentadiene; $\eta^4$-2,4-hexadiene; $\eta^4$-1,4-diphenyl-1,3-butadiene; $\eta^4$-3-methyl-1,3-pentadiene; $\eta^4$-1,4-dibenzyl-1,3-butadiene; $\eta^4$-1,4-ditolyl-1,3-butadiene; $\eta^4$-1,4-bis(trimethylsilyl)-1,3-butadiene, $\theta^4$-1-(4-t-butylphenyl)-4-phenyl-1,3-butadiene, $\eta^4$-1-(3-methylphenyl)- 4-phenyl-1,3-butadiene, or $\eta^4$-1-(3-methoxyphenyl)- 4-phenyl-1,3-butadiene;

R' is hydrogen or methyl, or one or two pairs of R' groups together cause the ring structure to be an indenyl, terahydroindenyl, fluorenyl or octahydrofluorenyl group;

R" is $C_{1-10}$ hydrocarbyl;

R'" is independently each occurrence hydrogen or $C_{1-10}$ hydrocarbyl;

E is independently each occurrence silicon or carbon; and m is 1 or 2.

10. A process according to claim 1 or 2 wherein the reaction is conducted in a polar, aprotic solvent.

11. A process according to claim 10 wherein the solvent is 1,2-dimethoxyethane, tetrahydrofuran or diethylether.

12. A process according to claim 10 wherein the reaction is performed in sequence in a single reactor vessel without isolation of intermediate products.

13. A process according to claim 2 wherein the oxidation is performed by use or a halogenated organic compound.

* * * * *